United States Patent [19]

Ausherman et al.

[11] Patent Number: 4,793,363
[45] Date of Patent: Dec. 27, 1988

[54] BIOPSY NEEDLE

[75] Inventors: Ronald W. Ausherman, Alton, Ill.; Richard A. Burkholder, St. Charles, Mo.

[73] Assignee: Sherwood Medical Company, St. Louis, Mo.

[21] Appl. No.: 906,358

[22] Filed: Sep. 11, 1986

[51] Int. Cl.$^4$ .................................................. A61B 10/00
[52] U.S. Cl. .................................. 128/754; 128/305; 604/165
[58] Field of Search ............... 128/749, 751-754, 128/305-305.1, 310; 604/165-166, 164

[56] References Cited

U.S. PATENT DOCUMENTS

| | | | |
|---|---|---|---|
| 1,248,492 | 12/1971 | Hill | 604/165 |
| 2,522,108 | 9/1950 | Flagg | 128/753 |
| 3,007,471 | 11/1961 | McClure, Jr. | 128/754 |
| 3,577,979 | 5/1971 | Van Der Gaast | 128/754 |
| 3,605,721 | 9/1971 | Hallac | 128/754 |
| 3,628,424 | 12/1971 | Jamshidi | 128/753 |
| 4,007,732 | 2/1977 | Kvavle | 128/754 |
| 4,163,446 | 8/1979 | Jamshidi | 128/754 |
| 4,249,541 | 2/1981 | Pratt | 128/753 |
| 4,262,676 | 4/1981 | Jamshidi | 128/753 |
| 4,266,555 | 5/1981 | Jamshidi | 128/753 |
| 4,403,617 | 9/1983 | Tretinyak | 128/754 |
| 4,445,893 | 5/1984 | Bodicky | 604/165 |
| 4,469,109 | 9/1984 | Mehl | 128/753 |
| 4,487,209 | 12/1984 | Mehl | 128/754 |
| 4,513,754 | 4/1985 | Lee | 128/753 |
| 4,532,935 | 8/1985 | Wang | 128/753 |
| 4,543,966 | 10/1985 | Islam | 128/754 |
| 4,609,370 | 9/1986 | Morrison | 128/754 X |
| 4,630,616 | 12/1986 | Tretinyak | 128/754 |
| 4,655,226 | 4/1987 | Lee | 128/754 |

Primary Examiner—Kyle L. Howell
Assistant Examiner—Angela D. Sykes
Attorney, Agent, or Firm—Stanley N. Garber; Andrew J. Beck; William R. O'Meara

[57] ABSTRACT

A bone marrow biopsy device is provided that includes a cannula member and a stylet member each having arcuate handles having a length greater than the width thereof, a luer lock connector, and a handle locking arrangement. The cannula member handle has a recess which receives a collar on the stylet member handle. A radial pin and an axially extending luer lock connector are disposed in the recess. The collar has a slot which receives the pin for locking the stylet and cannula members together.

24 Claims, 2 Drawing Sheets

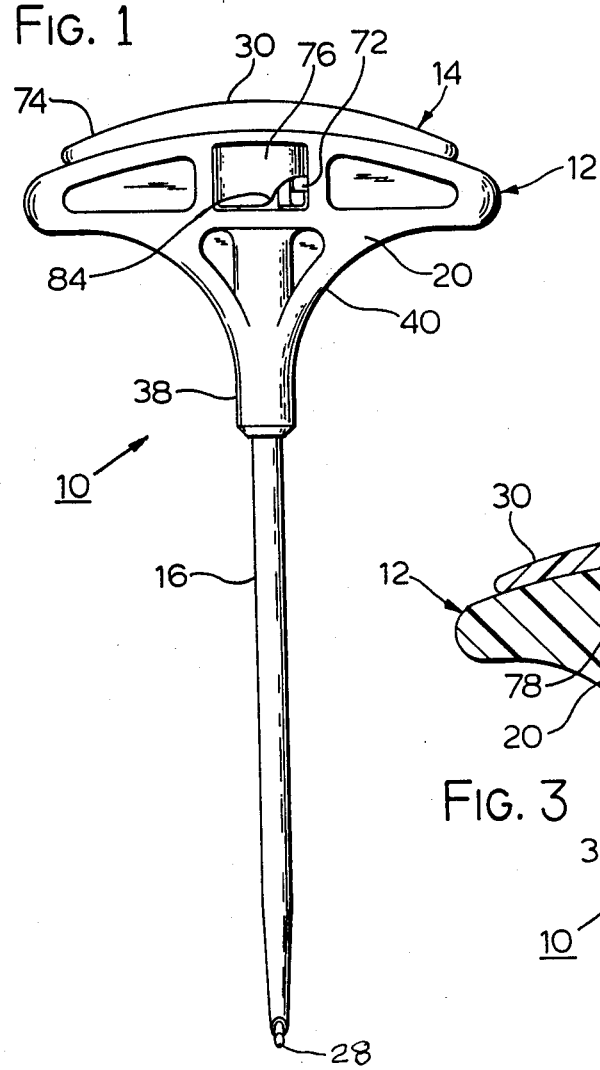
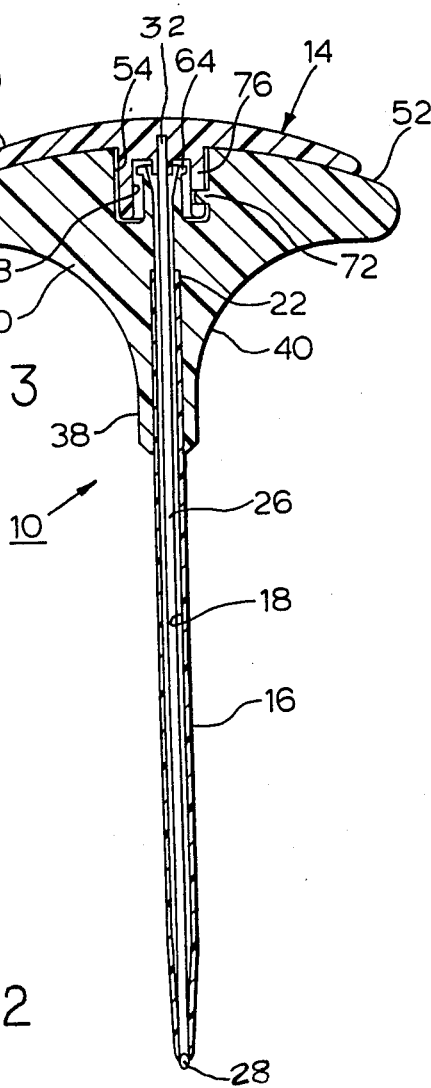
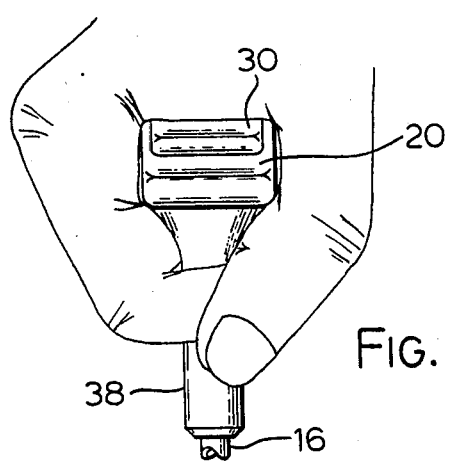

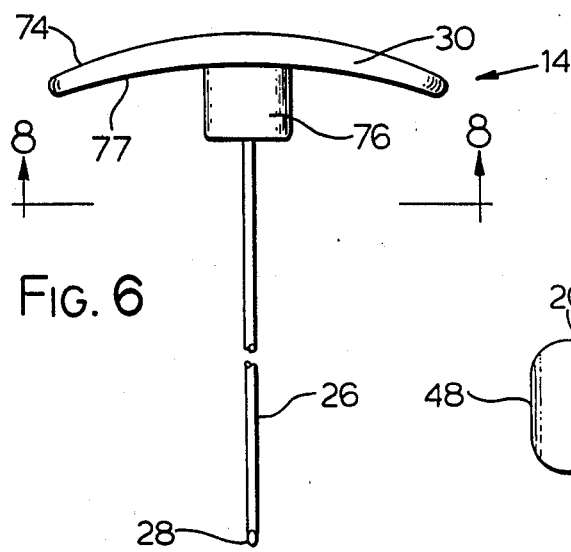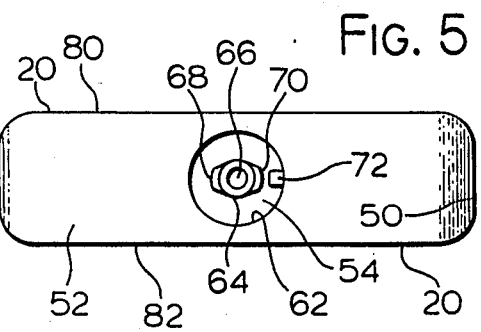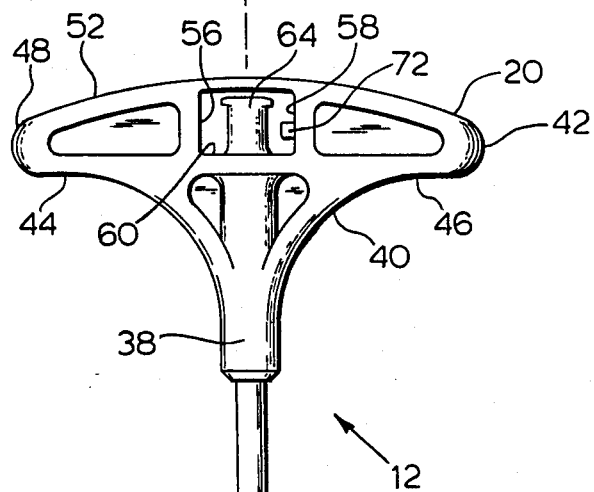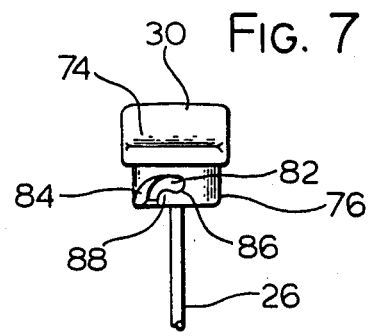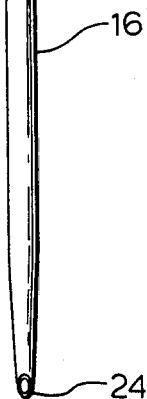

BIOPSY NEEDLE

TECHNICAL FIELD

This invention relates to biopsy needles and more particularly to bone marrow biopsy needles.

BACKGROUND ART

Some bone marrow biopsy needles are used to obtain bone marrow samples for diagnostic purposes as well as for harvesting marrow for transplant purposes. Such biopsy needles generally include a cannula member having a stainless steel cannula with a hub or handle connected to the proximal end of the cannula, and a stylet member having a stainless steel stylet and a handle or cap connected to the proximal end of the stylet. The cannula is provided with a sharp distal end and receives the stylet which is provided with a sharp pointed distal end that extends distally beyond the distal end of the cannula when the cannula and stylet members are assembled together for penetrating body tissue and bone in order to enter a bone marrow cavity, for example, the iliac crest of the patient. Both handles are hand grasped and considerable pressures are applied to cause the distal ends of the cannula and stylet to penetrate the tissue and bone.

Aspiration of a bone marrow sample is accomplished by removing the stylet member from the cannula member while the distal end of the cannula is in the marrow cavity. Then a syringe is connected to the proximal end of the cannula and marrow fluid is aspirated into the syringe. The aspirated sample is then processed for clinical testing. Where harvesting of marrow, such as for a transplant is desired, a relatively large number of biopsy needle insertions and marrow aspirations are generally required in order to accumulate a suitable amount of marrow. Where a biopsy core sample is to be obtained, the distal ends of the cannula and stylet are inserted into the marrow cavity and, after the stylet is removed, the cannula handle is rotated back and forth while applying axial pressure to the cannula to move the cannula through the marrow and collect a sample core within the cannula. The cannula is then carefully removed from the patient and the core sample pushed through the cannula and out the proximal end, such as by employing a probe. Aspirated samples and core samples may be taken from the same patient for a more complete diagnosis.

Good manual control of the biopsy device during insertion into the bone is necessary in order to avoid inadvertent damage to the patient. The size and shape of the upper portion of the biopsy device that is grasped by the hand of the practitioner, both with and without the stylet member in place, is an important consideration in providing good control of the device during use. Some biopsy devices have had handle portions which tend to concentrate the reaction forces during insertion to relatively small areas of the hand. This tends to produce discomfort or even damage to the practitioner and less control of the biopsy device because of the relatively high pressures applied to the device. This is especially the case where a considerable amount of bone marrow must be collected, such as in the case of a transplant, and a relatively large number of biopsies are required.

Some biopsy devices have employed a ball-type handle which engages a relatively small middle portion of the palm of the hand or a handle having protuberances which tend to concentrate the reaction force to relatively small areas of the palm. Some such devices, in general, have been uncomfortable to the practitioner especially where repeated samples are made. In some cases, when the stylet member was removed from the cannula member, the remaining handle of the cannula member had such a shape or had protuberances which produced discomfort to the practitioner.

Some such biopsy devices had handle locking constructions which produced undesirable protuberances which contacted the hand in use or constructions which could not readily use a luer lock connector for connecting the cannula to a syringe tip luer lock for aspiration of bone marrow fluid.

SUMMARY OF THE INVENTION

It is therefore an object of the present invention to provide an improved bone marrow biopsy device which substantially avoids one or more of the above-mentioned problems.

Another object is to provide an improved bone marrow biopsy device which has an upper portion adapted to be grasped by the hand of the practitioner which provides good manual control of the device during insertion into the bone of a patient and which minimizes discomfort to the practitioner.

Still another object is to provide a bone marrow biopsy device having cannula and stylet members and which provides good distribution of reaction forces to the hand during insertion into the patient and reduces discomfort to the practitioner when the device is used with and without the stylet member.

In accordance with the present invention, a bone marrow biopsy device is provided that includes a cannula member having a cannula and a handle connected to the proximal end of the cannula, and a stylet member having a stylet slidable in the cannula and a handle connected to the proximal end of the stylet. In one aspect of the invention, the upper surface of the cannula handle is arcuate. In another aspect, the upper surface of the stylet handle is arcuate. In accordance with another aspect, the handles are provided with releasable locking means which, when in locking engagement, are disposed within a recess in the cannula handle. In still another aspect, a luer connector is provided in a recess in the cannula handle for connecting another device with the cannula.

These, as well as other objects and advantages of the present invention will become apparent from the following detailed description and accompanying drawings.

BRIEF DESCRIPTION OF THE DRAWINGS

FIG. 1 is a side elevational view of a bone marrow biopsy device in accordance with a preferred embodiment of the invention;

FIG. 2 is a right side view of the upper portion of the device of FIG. 1 showing a portion of a hand grasping the device;

FIG. 3 is a longitudinal cross-sectional view of the device of FIG. 1;

FIG. 4 is a side elevational view of the cannula member, alone, of the device of FIG. 1;

FIG. 5 is a top plan view of the cannula member as shown in FIG. 4;

FIG. 6 is a side elevational view of the stylet member, alone, of the device of FIG. 1 but rotated 180° about its longitudinal axis.

FIG. 7 is a left side view of the upper portion of the stylet member as shown in FIG. 6; and FIG. 8 is a bottom plan view of the stylet member as shown in FIG. 6.

DESCRIPTION OF THE PREFERRED EMBODIMENT

Referring now to the drawings and more particularly to FIGS. 1-3, a bone marrow biopsy device 10 is shown including a cannula member 12 and a complementary stylet member 14 in assembly relation for use in performing a bone marrow biopsy.

The cannula member 12, as shown also in FIGS. 4 and 5, includes a metal cannula 16, for example, of stainless steel, having a lumen 18 extending through the cannula, and a handle 20 connected to the proximal end, indicated at 22 in FIG. 3, of the cannula. The distal end of the cannula 16, indicated at 24, is formed at an angle to the longitudinal axis of the cannula and is shapened for passing through tissue and bone marrow. The handle 20 is preferably a unitary, molded plastic member fixed to the cannula 16, such as by suitable adhesive, for example, an epoxy resin. Preferably, handle 20 is formed of a relatively hard plastic, such as a copolymer made from acrylonite, butadiene and styrene (ABS).

Stylet member 14, shown also in FIGS. 6-8, includes a solid metal stylet 26, for example, of stainless steel, having a pointed and sharpened distal end 28, and a stylet handle 30 fixed to the proximal end of the stylet 26 indicated at 32 in FIG. 2. The stylet handle 30 may also be molded of a suitable plastic, preferably a relatively hard plastic such as ABS. The stylet 26 is fixed to handle 30 such as by a suitable adhesive, for example, an epoxy resin.

When stylet member 14 is disposed within the cannula member 12 and is in a fully inserted or assembled condition as shown in FIGS. 1 and 2, the handles 20 and 30 are engaged and the pointed distal end 28 of the stylet 26 extends slightly beyond the distal end 24 of the cannula 16.

The cannula handle 20 has a generally cylindrical lower portion 38 integrally connected with an upwardly and radially outwardly extending conical portion 40. The conical portion 40 smoothly connects with a radially outwardly extending integral upper member 42 having opposed bottom wall portions 44 and 46 respectively, of the handle. Bottom wall portions 44 and 46 smoothly connect with opposed rounded ends 48 and 50 respectively, which, in turn, smoothly connect with the upper surface of an upper wall 52 which is arcuate from one end to the other. As best seen in FIG. 5, the width of the upper surface or wall 52 is relatively narrow compared to the length of the top wall, as will be further discussed hereafter. A channel or recess 54 having opposed, distally extending, laterally spaced walls 56 and 58 and a bottom wall 60 (FIG. 4) is formed in the upper member 42 and wall 52. The recess 54 has an upper opening 62 of less diameter than the width of the upper wall 52 so that the upper wall 52 extends continuously from one opposed end 48 to the opposite end 50. Integrally connected to the bottom wall 50 is a luer lock connector 64 which extends upwardly along the longitudinal axis of the cannula member 12 but terminates below the upper surface of upper wall 52. Luer lock connector 64 includes a luer slip connector bore or socket 66 which connects with the lumen 18 of cannula 16. Luer connector 64 is provided with a pair of opposed ears 68 and 70 (FIG. 5) which serve as coupling threads adapted to be threaded into a complementary conventional luer lock connector of a device such as syringe for connecting the syringe to the cannula 16 for aspirating marrow fluid. Extending radially inwardly from sidewall 58 of recess 54 is a camming and handle locking pin 72 which extends normal to the longitudinal axis of the cannula member 12 and terminates in laterally spaced relation from the luer lock connector 64.

The stylet member handle 30 includes an upper arcuate wall 74 having an integral hub or collar 76 depending axially from a bottom wall 77 of the handle 30 and is shown generally cylindrical and concentric with the stylet 26. The bottom wall 77 of handle 30 is also arcuate and complementary to the arcuate upper surface 52 of the cannula handle 20 so that when the stylet member 14 is fully disposed within the cannula member 12 as shown in FIGS. 1 and 2, the lower wall 77 engages and generally conforms to the upper wall 52 with the walls 52 and 78 in nesting relation and in contact with each other over substantial areas. The radius of the arc of the bottom wall 77 is approximately the same as the arc of the upper surface of wall 52. The collar 76 has inner sidewalls 78 (FIGS. 3 and 8) dimensioned to receive the luer lock connector 64 without interference as best seen in FIG. 3. Concentric with the sidewalls 78 is an integral needle hub 80 as seen in FIGS. 3 and 8 and to which the stylet 26 is secured to the handle 30 such as by suitable adhesive, for example, an epoxy resin.

A cam and locking slot or groove 82, as best seen in FIGS. 1, 7 and 8 is formed in the sidewall of stylet collar 76, the groove 82 being open to the bottom edge of the collar. When the stylet 14 is placed within the cannula member 12, the collar 76 receives the luer lock connector 64 without interference and can be rotated so that pin 72 of cannula handle 20 enters the groove 82. Groove 82 has an entrance at the bottom of the collar 76 and a curving cam wall 84, as best seen in FIGS. 7. The cam wall 84 of the groove 82 extends angularly upwardly and laterally and connects with a lateral slot portion 86 having a somewhat resilient protrusion 88 at the entrance to the slot portion 86 tending to reduce the width of the slot to prevent the camming pin 72 from inadvertently moving from the slot portion 86 and out of the collar.

When the stylet member 14 is inserted into the cannula member 12 and rotated, such as in a clockwise direction, the pin 72 enters the groove 82 and engages camming portion 84 causing the stylet 14 to move downwardly, and as the pin 72 is forced past protrusion 88, it enters the locking slot portion 86 and engages the end wall of the slot. The groove 82 and pin 72 are constructed such that when the stylet handle 30 is sufficiently rotated, it will be in parallel relation with the handle 20 of the cannula member as shown in FIGS. 1 and 2 and with the handles in close contacting relation. The lower surface 77 of the stylet handle 30 will preferably be in some frictional engagement with the upper surface 52 of handle 20 of the cannula member and the pin will be in the locking portion of slot 82 so that such frictional engagements will lock the handles 20 and 30 in proper orientation, that is, as shown in FIGS. 1 and 2. This is the position and relationship of the handles when the biopsy device is to be used to pass through body tissue and a sidewall of a bone in order to enter the bone cavity. In the assembled position of FIG. 1, the cannula 16, stylet 26, luer connector bore 66, socket 78, recess 56 and collar 76 are all concentrically related with the recess 56 and the collar 76 located equidistant from the opposed ends of the handles.

When it is desired to remove the stylet member 14 from the cannula member 12, the stylet handle 30 is rotated, for example, in a counter-clockwise direction relative to the handle 20, so that the collar 76 is moved relative to pin 72 such that the pin 72 moves out of locking groove portion 86, past protrusion 88, and into camming engagement with cam surface 84. This camming engagement causes the stylet handle 30 to move upwardly as it is rotated thereby lifting the stylet handle 30 away from the upper surface 52 of the cannula handle 20 making it easy to then fully grasp the handle 30 and pull the stylet member 14 longitudinally upwardly and out of the cannula member 12.

In use, with the cannula members secured together, as is shown in FIG. 1, the handles 20 and 30 are grasped by the hand with the upper surface 52 engaging the palm of the hand and with the cylindrical portion 38 and conical portion 40 between fingers of the hand, such as shown in FIG. 2. The longer lengthwise dimensions of the upper wall 52 of the cannula handle when hand held extends laterally across the width of the palm, that is, normal to the longer axes of of the fingers. As seen in FIG. 2, the width of the cannula handle or wall 52 is approximately the same as the distance between the thumb and index finger, and this enhances handling comfort.

The upper arcuate exterior surfaces of the upper walls 52 and 74 of the cannula and stylet handles are flat and, as shown, are continuous from one end to the other. Also, there are no protuberances extending proximally or above the upper surfaces of these walls. Preferably, the upper peripheral edges defining the upper surfaces are smoothly rounded to avoid any sharp edge that would engage the hand of the person using the device 10. Since the palm of the hand is generally arcuate in the width direction, the arcuate upper walls 52 and 74 closely fit the palm and contact a large surface area for good distribution of forces and comfort.

The length of the upper surface of wall 52 of the cannula handle 20, that is, the arc length between the opposed ends 48 and 50 is substantially greater than its width, that is, the distance between the opposed sides indicated at 80 and 82 in FIG. 5. Preferably, the length of wall 52 is at least twice that of its width and even more preferably three to four times the width. It has been found that when the length of the wall 52 is approximately that of the width of the palm of the average sized hand and the width of the wall is between about one-half and one inch, and the wall is arcuate, the reaction forces resulting from the insertion of the distal ends of the cannula and stylet through body matter are greatly distributed across relatively large areas of the palm, and the handle 20 fits comfortably in the hand. The length of the upper wall 52 may be between about 2 and 3½ inches, preferably about 3 inches while the width is preferably about 7/8 of an inch. When the width is about ⅞ of an inch it especially snugly fits between the thumb and index finger when gripped as shown in FIG. 2.

The upper wall 74 of the stylet handle 30 is also substantially of greater length than its width, that is, its arc length between opposed ends 80 and 82 (FIG. 8) is greater than its width as measured between its sides 84 and 86. Preferably the length is at least twice its width and even more preferably three to four times its width. The width may be between ½ and ⅞ of inch and the length between about 1½ and 3 inches. Preferably, the width and length of the upper wall 74 are somewhat less than those of the upper wall of the cannula wall 52 as shown. A highly desirable width of about 11/16 inch with a length of about 2½ inches.

With these preferred dimensions, the handles 20 and 30 when assembled as well as when only the cannula is employed, provide a comfortable fit in the arcuate palm of the hand. Also, forces acting on the palm are distributed across a substantially large area of the palm and this reduces discomfort and produces good hand control and which are especially important where a number of biopsy samples are to be taken by the same person.

With the present construction, there are no protuberances extending above the upper surfaces of either of the handles 20 and 30 that would otherwise produce discomfort or even damage to the hand of the user yet good handle locking arrangement and a luer lock connector are provided.

With the luer connector 64 disposed in the recess 56 provided in the upper wall of the cannula handle 20, it can be provided with luer lock ears 68 and 70 so that an aspiration syringe tip or the like with a luer lock connector can be fitted around the connector 64 to provide a locked connection between the syringe and the connector. Also, since the cam handle locking pin is also within the recess 54 it does not effect a protrusion that would be engaged by the hand. Also, the luer lock connector 64 does not interfere with the cooperable handle locking pin member 72 in the recess 54 and the groove 82 in stylet collar 74.

When it is desirable to obtain a biopsy sample, the device 10, as shown in FIG. 1, is grasped and may be held in the palm of the hand as shown in FIG. 2. The distal ends are then forced through body tissue and the wall of a bone. When aspiration of bone marrow is desired, the distal end 24 of cannula 16 is maintained within the bone, the stylet member 14 removed from the cannula member 12 as previously described, and a syringe luer tip, with or without a luer lock, may then be connected to the luer lock connector 64. The syringe piston can then be moved so that bone marrow fluid will flow in the cannula 16 and into the syringe. Where a biopsy core cample is desired, the device 10, as shown in FIG. 1, is inserted just through the wall of the bone and the stylet member 14 is removed from the cannula member 12 while the distal tip of the cannula 16 is within the bone cavity. Then, the cannula handle 20 is grasped alone and the cannula is forced through the bone marrow resulting in a core of the marrow within the cannula. The cannula member 12 is removed from the patient and the core removed from the cannula 16.

As various changes could be made in the above described construction without departing from the true spirit and scope of the invention, it is intended that all matter contained in the above description and shown in the accompanying drawings be interpreted as illustrative.

What is claimed is:

1. A bone marrow biopsy device comprising a cannula member having upper proximal and lower distal ends and including a cannula open at the proximal and distal ends, and a handle connected to said cannula at the proximal end thereof, and a stylet member having upper proximal and lower distal ends and including a stylet having a pointed distal end, and a handle connected to said stylet at the proximal end thereof, said stylet being slidable in said cannula and removable from said cannula member, said stylet member handle including an upper wall having a length substantially greater than the width thereof, said upper wall having an upper surface generally arcuate in the lengthwise direction thereof and substantially flat in the widthwise direction thereof.

2. The device of claim 1 wherein said upper surface is continuous from one end to the other end and is free of any protuberance extending above said upper surface.

3. The device of claim 1 wherein the length of said stylet member handle is at least twice that of the width thereof.

4. The device of claim 1 wherein the length of said stylet member handle is between about 3 and 4 times the width thereof.

5. The device of claim 1 wherein the upper surface of said cannula member has a length approximately equal to the width of an average-sized hand.

6. The device of claim 1 wherein the length of said generally arcuate upper surface is greater than 2 inches.

7. The device of claim 6 wherein the width of said generally arcuate surface is less than one inch.

8. The device of claim 7 wherein the width of said arcuate surface is greater than one-half inch.

9. The device of claim 1 wherein said cannula member handle has an upper wall with an upper surface substantially longer than the width thereof and is generally arcuate in the lengthwise direction.

10. The device of claim 9 wherein the major portion of a lower surface of said stylet member upper wall is arcuate in the lengthwise dimension thereof and is engageable with said upper arcuate surface of said cannula member handle when said stylet is fully in said cannula.

11. The device of claim 10 wherein said cannula member handle has a generally conical portion depending therefrom and with said cannula extending coaxially with the conical portion.

12. The device of claim 11 wherein the radius of the arc defined by said generally arcuate upper surface of said cannula member handle upper wall is substantially the same as that of the arc defined by said arcuate bottom surface of said upper wall of said stylet member handle so that portions of said upper arcuate surface of said cannula handle upper wall nest within the lower arcuate surface of said upper wall of said stylet member handle when said cannula and stylet member handles are engaged for use.

13. The device of claim 9 wherein the upper surface of each of said walls is continuous between the opposed ends thereof and free of any protuberances extending proximally from said surfaces, said upper wall of said cannula member being substantially flat in the widthwise direction, said cannula handle having a recess midway between the opposed ends thereof, said stylet handle having a distally extending portion midway between the opposed ends thereof movable into said recess, first and second complementary locking means respectively on the sidewall of said recess and on said distally extending portion for locking said handles together in a locked condition with said handles in engagement with each other and said upper surfaces of said walls extending in parallel relation with each other.

14. The device of claim 13 wherein said distally extending portion includes a collar, said first locking means includes a pin connected to the sidewall of said recess and extending radially inwardly therefrom, said second locking means includes a groove open at the distal end of said collar for receiving said pin when said collar is moved into said recess and rotated in a predetermined direction, said groove having a closed end engagable with said pin to limit relative rotation in said locked condition.

15. The device of claim 14 wherein said cannula handle includes a luer lock connector extending proximally in said recess with the proximal end thereof distally of the upper surface of said cannula handle, said connector having a luer tapered bore extending therethrough, said collar surrounding said connector when said handles are in said locked condition.

16. The device of claim 15 wherein said connector includes a pair of radially outwardly extending luer lock ears at the proximal end of said connector within said recess.

17. The device of claim 13 wherein the length of each of said upper walls is between three and four times the width thereof, and said cannula member upper wall is longer and wider and engageable with a lower side of said stylet handle member upper wall.

18. The device of claim 9 wherein the upper surface of the upper wall of said cannula member handle is substantially flat in the widthwise direction, continuous between the opposed ends thereof, and free of any protuberances extending proximally therefrom.

19. The device of claim 1 wherein said cannula member handle has a recess extending distally from the upper surface thereof, luer connector means including a luer tapered bore in said recess coaxial with said cannula for receiving a complementary luer tapered connector adapted for connection with said cannula, and locking means for coupling said handles together with said handles in contact with each other and extending in parallel relation.

20. A bone marrow biopsy device comprising a cannula member having upper proximal and lower distal ends and including a cannula open at the proximal and distal ends, and a handle connected to said cannula at the proximal end thereof, said cannula handle having an upper wall with a recess extending distally and coaxially with said cannula, and a stylet member having upper proximal and lower distal ends and including a stylet having a pointed distal end, and a handle connected to said stylet at the proximal end thereof, said stylet being slidable in said cannula and removable from said cannula member, said stylet member handle having an upper wall and a depending collar movable into said recess, pin means in said recess extending generally radially inwardly from a sidewall of said recess, a groove in the sidewall of said collar with an entrance to said groove at the distal end of said collar so that said pin means can enter said groove when said collar is inserted into said recess for holding said members together, said upper walls of said cannula and said stylet handles each having an upper surface with a length substantially greater than the width thereof and generally arcuate in the lengthwise direction and free of any protuberances extending upwardly therefrom, the uppermost point on each of said upper surfaces being substantially at the longitudinal axis of said stylet.

21. The device of claim 20 wherein said groove includes a cam surface engagable with said pin means in response to rotation of said stylet handle in one direction to effect axial proximal movement of said stylet handle relative to said cannula handle.

22. The device of claim 20 including an upstanding luer connector within said recess and coaxial with said cannula, said connector having an inner luer tapered bore open at both ends and adapted to receive a luer tapered connector of another device for connecting the other device with said cannula.

23. The device of claim 22 wherein said luer connector includes radially outwardly extending luer lock thread means in said recess for locking engagement with a complementary luer lock connector.

24. The device of claim 20 wherein the lower surface of said stylet handle is arcuate in the lengthwise direction and in nesting relation with the upper surface of said cannula handle when said handles are in engagement.

* * * * *